United States Patent
Morrison et al.

[11] Patent Number: 5,879,694
[45] Date of Patent: Mar. 9, 1999

[54] TRANSPARENT GEL CANDLES

[75] Inventors: David S. Morrison, The Woodlands; William J. Heilman, Houston, both of Tex.

[73] Assignee: Pennzoil Products Company, Houston, Tex.

[21] Appl. No.: 798,946

[22] Filed: Feb. 11, 1997

Related U.S. Application Data

[62] Division of Ser. No. 520,726, Aug. 29, 1995, abandoned.

[51] Int. Cl.⁶ .................................................. A01N 25/08
[52] U.S. Cl. ........................ 424/405; 424/400; 424/409; 424/411; 424/78.31; 44/269; 431/288; 514/919
[58] Field of Search .......................... 44/269–272, 275, 44/572; 431/288, 289, 292; 424/400, 405, 409, 411, 420, 40, 78.31–78.38, DIG. 10, 919

[56] References Cited

U.S. PATENT DOCUMENTS

| | | |
|---|---|---|
| 3,437,462 | 4/1969 | Maloney . |
| 3,437,464 | 4/1969 | Maloney . |
| 3,850,586 | 11/1974 | Iwama et al. . |
| 3,857,805 | 12/1974 | Prickril ............................... 260/28.5 B |
| 4,369,284 | 1/1983 | Chen . |
| 4,621,111 | 11/1986 | Duvdenvani et al. . |
| 5,132,355 | 7/1992 | Nahlovsky . |
| 5,143,723 | 9/1992 | Calvo et al. .............................. 424/63 |
| 5,221,534 | 6/1993 | DesLauriers et al. ............... 424/78.03 |
| 5,395,233 | 3/1995 | Karp . |
| 5,578,089 | 11/1996 | Elsamaloty ............................... 44/275 |

FOREIGN PATENT DOCUMENTS

| | | |
|---|---|---|
| 224389 | 6/1987 | European Pat. Off. . |
| 61-98780 | 5/1986 | Japan . |
| WO88/00603 | 7/1987 | WIPO . |
| WO96/34077 | 10/1996 | WIPO . |

*Primary Examiner*—Neil S. Levy
*Attorney, Agent, or Firm*—McDermott, Will & Emery

[57] ABSTRACT

Transparent stiff gel candles comprising a hydrocarbon oil, a wick, and one or more triblock, radial block or multiblock copolymer of a thermoplastic rubber, and optionally a diblock copolymer.

10 Claims, 1 Drawing Sheet

TRANSPARENT GEL CANDLES

This application is a division of application Ser. No. 08/520,726 filed Aug. 29, 1995, abandoned.

TECHNICAL FIELD

This invention relates to candles in the form of firm gels, and more particularly to stiff heterophase, thermally reversible mineral oil gels, preferably white oil gels. The candles of the invention contain block copolymers and blends thereof, the copolymers being preferably derived from styrene-rubber block units. The candles are naturally transparent and uncolored. Optionally, the candles may be colored with one or more colors, and may contain embedded and/or external ornamental features, as well as fragrances and functional additives.

BACKGROUND ART

Candles made of conventional waxes are well known. A major decorative drawback to such a candle is that the use of waxes necessitates that the candle be opaque, thus limiting the ornamental capacity of the candle with respect to embedded decorative features.

Clear oil jar candles are also known in the art. However, prior to the present invention, these candles have been in liquid form only. These clear liquid candles, while permitting a type of embedded ornamental feature, do not permit the shaping of, for example, a pillar candle. These liquid candles are known to accumulate dust and other particulate matter from the air, thereby requiring that the oil be periodically discarded for aesthetic reasons. Additionally, liquid oil candles may spill and damage furnishings and the like. As yet another drawback, liquid candles must be assembled by the user.

U.S. Pat. No. 5,395,233 discloses a process for producing a potpourri wax candle. While such a candle has a decorative feature embedded therein, it is of a complex layered structure, and thus not easily manufactured.

U.S. Pat. No. 5,132,355 discloses a polyethylene block copolymer gelling agent, which may be used as a base for a decorative molded candle. This candle, however, is not transparent, and thus is of limited decorative value.

The present invention overcomes the problems in the prior art by providing stiff gel candles that are transparent. Thus, the candles of the invention permit the decorative shaping advantages of conventional wax candles as well as the embedded ornamental advantages of liquid oil candles. The candle of the present invention therefore provides an improved substitute for the conventional wax pillar or jar candle and for liquid oil jar candles.

The present invention involves a new use for oil-containing block copolymer gels as the hydrocarbon source of a candle. There is a need in the art for candles with improved aesthetic properties. Stiff transparent candles, into which decorative features have been added, are particularly desired. Accordingly, in this invention, advantageous combinations of block copolymers and oils are provided which produce heterophase thermally reversible mineral oil gels, and which have desirable properties for application as a clear, stiff gel candle.

The current methodology for producing mineral oil containing gels includes the use of metal soaps, surfactants (microemulsions), homopolymers, ionic homo- and copolymers and block copolymers. Some common gelling agents are fatty acid soaps of lithium, calcium, sodium, aluminum, zinc and barium. A number of homo- and copolymers have been used to gel hydrocarbon systems at certain polymer treatment levels including atactic ethylene-propylene. Homopolymers or copolymers which have pendant salt groups also form ion rich aggregates in a non-polar matrix. The ionic interaction and resultant polymer properties of these compositions, however, are dependent on the type of polymer backbone, type of ionic moiety and type of cation. Sulfonated polystyrenes exemplify this kind of system. Surfactant combinations have also been used to gel mineral oil/water systems. Surfactants are used at about 30 weight percent to gel oil and to gel 1:4 oil and water mixtures. Nonionic surfactants such as polyoxyethylene sorbitan monooleates exemplify these type of systems.

Block copolymers are also known to provide physical cross-links to gels by selective sulfonation and subsequent phase separation of a particular block. Block systems including styrene-isoprene, styrene-butadiene and styrene ethylene oxide copolymers have been used for this cross-linking.

The advantages of the candle of the invention, which are set forth below or easily recognized by those of ordinary skill in the art, are provided by use of firm heterophase, thermally reversible mineral oil gels as the hydrocarbon portion of the candle.

SUMMARY OF THE INVENTION

It is accordingly one object of this invention to provide heterophase, thermally reversible still gel compositions which have advantageous properties when used as a candle, preferably a clear jar candle.

A further object of the invention is to provide stiff hydrocarbon oil gel compositions formed from certain triblock, radial block and/or multiblock copolymers, and optionally a diblock copolymer, which have advantageous properties when used as a candle.

A still further object of the invention includes a method for making a transparent or colored candle comprising a heterophase thermally reversible mineral oil gel, using triblock, radial block and/or multiblock copolymers, optionally in conjunction with a diblock copolymer. The copolymers are preferably based on thermoplastic rubbers such as styrene-rubber block copolymers.

Other objects and advantages of the present invention will become apparent as the description thereof proceeds.

In satisfaction of the foregoing objects and advantages, there is provided by the present invention a transparent or colored candle comprising:

(a) a hydrocarbon oil; and (b) at least one block copolymer selected from the group consisting of:
  1) a triblock copolymer;
  2) a radial block copolymer;
  3) a multiblock copolymer; and (c) optionally, a diblock copolymer, and (d) a wick, said candle further optionally comprising a stabilizer, anti-oxidizing agent, colorant, fragrance, and/or functional additive, and the like.

BRIEF DESCRIPTION OF DRAWINGS

Reference is now made to the drawings accompanying the application wherein:

FIG. 1 depicts a clear jar candle under one embodiment of the invention.

DESCRIPTION OF THE INVENTION

Figure 1:
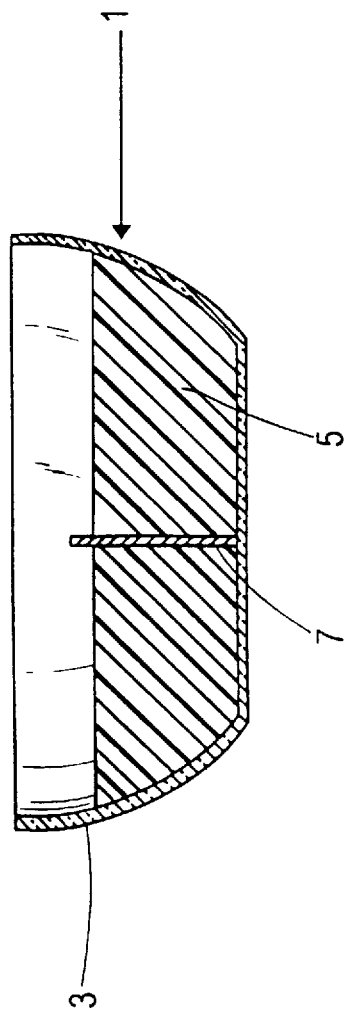
FIG. 1.

It has been discovered according to the present invention that by controlling the degree of physical crosslinking exhibited in block copolymers, heterophase thermally reversible mineral oil gels can be formed which have desirable properties for use as candles. In particular, it has been found that such gels provide for stiff, transparent candles.

Under the invention, the gel consistency of the candle is controlled by varying the amount, ratio and types of certain polymers, preferably triblock, radial block and/or multiblock copolymers, and optionally a diblock copolymer, to provide gels which have desirable rheological properties and thus provide for a novel firm candle. Accordingly, the present invention provides a candle that is intrinsically transparent, yet may be colored through the use of one or more colorant, if desired. The candles of the invention are preferably jar candles, and in particular transparent jar candles.

According to the invention, it has been discovered that triblock, radial and/or multiblock copolymers, optionally in conjunction with a diblock copolymer, yield a tightly crosslinked, stiff gel.

Product formation is achieved from block copolymers which will form three-dimensional networks or gels through physical crosslinks. Crosslinking in these block copolymers occurs due to the formation of sub-microscopic particles of a particular block, referred to as domains. Crosslinking of the insoluble domains can be obtained by factors affecting the crosslink density of the networks including length of insoluble block domains, length of soluble block domains, and the number of crosslinkable sites. For example, branched or star polymers and other multiblock copolymers will have more crosslinks than triblock or diblock polymers. The type of solvent or plasticizer to which the blocks are subjected will also affect these characteristics.

Certain gels exhibit syneresis wherein the separation of liquid from the gel by contraction occurs by virtue of the concentration of the insoluble block present in the triblock copolymer. The higher the concentration of the insoluble block, as exemplified by styrene, the more phase separation and crosslinking will occur. However, according to this invention, it has further been discovered that the amount of syneresis which occurs can be controlled by mixing such systems with triblock, radial block and/or multiblock copolymers, and optionally diblock copolymers, which do not exhibit syneresis.

The composition of the present candles utilizes a mixture of polymers in combination with a hydrocarbon oil. Preferably the hydrocarbon oil is white oil. Other oils, including but not limited to refined, aromatic-free paraffinic and naphthenic oils, solvents, synthetic liquid hydrogenated or unhydrogenated oligomers of, for example, polybutene, polypropylene, polydecene and polyterpene, are also useful in the candle of the invention.

The polymers used comprise at least one copolymer selected from the group consisting of triblock, radial block and/or multiblock copolymer, and mixtures thereof, and optionally a diblock copolymer. It is required, however, that at least one triblock block, radial block or multiblock copolymer be present in the candle composition.

Each of the triblock, radial block and/or multiblock copolymers in the invention contains at least two thermodynamically incompatible segments. By the expression thermodynamically incompatible with respect to the polymers, it is meant that the polymer contains at least two incompatible segments, for example at least one hard and one soft segment. In general, in a triblock polymer, the ratio of segments is one hard, one soft, one hard or an A-B-A copolymer. The multiblock and radial block copolymers can contain any combination of hard and soft segments, provided that there are both hard and soft characteristics. In the optional diblock copolymer, the blocks are sequential with respect to hard and soft segments.

Commercially available thermoplastic rubber type polymers which are especially useful in forming the compositions of the present invention are sold under the trademark Kraton® by Shell Chemical Company. The Kraton® rubber polymers are described as elastomers which have an unusual combination of high strength and low viscosity and a unique molecular structure of linear diblock, triblock and radial copolymers. Each molecule of the Kraton® rubber is said to consist of block segments of styrene monomer units and rubber monomer and/or comonomer units. Each block segment may consist of 100 or more monomer or comonomer units. The most common structure is the linear ABA block type; styrene-butadiene-styrene (SBS) and styrene-isoprene-styrene (SIS), which is the Kraton® D rubber series.

A second generation polymer of this general type is the Kraton® G series. This copolymer comprises a styrene-ethylene-butylene-styrene type (S-EB-S) structure. The Kraton® G series is preferred in the practice of the invention, as the copolymers of this series are hydrogenated and thus more thermally stable; that is, decomposition is less likely to occur during blending of the G series polymers with the oil (the D series polymers having unsaturation within the rubber block). The Kraton® G rubbers are indicated as being compatible with paraffinic and naphthenic oils and the triblock copolymers are reported as taking up more than 20 times their weight in oil to make a product which can vary in consistency from a "Jello®" to a strong elastic rubbery material depending on the grade and concentration of the rubber.

The optionally blended diblock polymers include the AB type such as styrene-ethylenepropylene (S-EP) and styrene-ethylenebutylene (S-EB), styrene-butadiene (SB) and styrene-isoprene (SI).

The ABA structure of the Kraton® rubber molecule has polystyrene endblocks and elastomeric midblocks. This series of polymers is indicated as being a compounding ingredient or additive in adhesives, sealants and coatings, asphalt modification for roads and roofing, polymer modification, thermoset modification, and oil modification including use as viscosity index improvers, greases and gels. Certain grades of the Kraton® D series are also indicated as being useful as viscosity modifiers for formulating multigrade motor oils.

International Patent Application No. WO88/00603, published Jan. 28, 1988, by Francis et al. describes block copolymers which can be used as one or more components in the present invention. These block copolymers are described as gels or gelloid liquid extended polymer compositions which can comprise an intimate mixture of a block copolymer containing relatively hard blocks and relatively elastomeric blocks. The additional polymer or copolymer material has at least partial compatibility with, and a higher glass transition softening or melting temperature than, the hard blocks of the block copolymer. The copolymer additionally has at least 500 parts by weight of extender liquid per 100 parts of the block copolymer, the liquid being present to extend and soften the elastomeric blocks of the block copolymer. The extender liquid can be a hydrocarbon oil and/or a synthetic oil. These gels or gelloid compositions are an example of the type of gel which can be used in the candles of the present invention. The entire disclosure of this published application is incorporated herewith.

International Patent Application No. W088/00603 also refers to European Patent Application No. 224389 of Garmarra et al, published Jun. 3, 1987. This European patent application discloses styrene-diene block copolymer compositions and in particular discloses a mixture of triblock copolymers and a hydrocarbon oil, wherein the mixture of triblock copolymers comprises a triblock polymer having (a) styrene to ethylene-butylene ratio of 14 to 30 styrene blocks to 70 to 86 ethylene-butylene blocks, and (b) ethylene-butylene ratio of 31 to 35 styrene blocks to 65 to 69 ethylene-butylene blocks, and wherein the ratio of copolymer A to copolymer B is from about 15 to 85 to about 85 to 15. These compositions are said to be particularly useful as sealing materials. Block copolymers of the type described in this published European application may also be used to make the candles of the invention. The disclosure of European Patent Application No. 224389 is also incorporated herein by reference.

U.S. Pat. No. 5,221,534 discloses gels having a mineral oil and blends of di- and triblock copolymers. These gels are useful for health and beauty aid compositions. These health and beauty aid compositions contain at least two diblock or triblock copolymers and an effective amount of one or more cosmetic ingredient. Preferred compositions in U.S. Pat. No. 5,221,534 contain both diblock and triblock copolymers, with the polymer blend being from about 5 to 95 wt % of diblock polymer to 95 to 5 wt % of triblock polymer. The gel disclosed in U.S. Pat. No. 5,122,534, without the cosmetic additive, may also be used in the candle of the invention. The entire disclosure of U.S. Pat. No. 5,221,534 is also incorporated herein by reference.

U.S. Pat. No. 4,369,284 describes a transparent gel prepared from triblock copolymers and oils, including food and technical grade white petroleum mineral oils. The triblock copolymers therein give specific styrene end blocks to ethylene and butylene center blocks. The end block to ethylene and butylene center block ratio is given as being between 31:69 and 40:60. It is preferred under the present invention, however, that the end block to ethylene and butylene center block ratio be less than 31:69. The polymer content in the Examples of U.S. Pat. No. 4,369,284 is from 5.9 to 25 percent. The disclosure of U.S. Pat. No. 4,369,284 is incorporated herein in its entirety.

U.S. Pat. No. 5,132,355 discloses polyethylene block copolymers of the A-B-A type, where in A is a "hard" block and B is a "soft" block. The gel made from this diblock copolymer is disclosed as being useful for complex molded candles when used with paraffin wax.

In the preferred embodiment of the present invention, the polymer or polymer blend is formed in admixture with a carrier vehicle such as a natural or synthetic hydrocarbon oil or mixtures thereof. The hydrocarbon oil may be a paraffinic oil, a naphthenic oil, natural mineral oil or the like. White oil is particularly preferred.

When formed into gels, the copolymers or blends thereof will comprise from about 2 to about 30 weight percent of the total weight of the composition. Preferably the total weight of polymer contained in the oil will range from about 3 to about 20 weight percent, and may range from about 5 to about 15 weight percent, or more preferably from about 7 to about 12 weight percent. Most preferably the total weight of the copolymer in the invention is about 8.6 weight percent.

The formulation for the products of the invention will comprise about 70 to about 98 weight percent of the hydrocarbon oil or carrier vehicle, about 2 to about 30 weight percent of the triblock, radial block, multiblock copolymers, and optionally from 0 to about 10 weight percent diblock copolymer.

A preferred composition of the invention will contain from about 4 to about 20 weight percent of the polymer blend and from about 80 to about 96 weight percent of a suitable hydrocarbon oil, preferably white oil. The preferred polymer is a triblock polymer of the Kraton® G type, in particular Kraton® G-1650.

Kraton® G-1650 is an SEBS triblock copolymer which has a specific gravity of about 0.91, and is said to have a tensile strength of about 500 psi as measured by ASTM method D-412-tensile jaw tester separation speed 10 in/min. The styrene to rubber content of Kraton® G-1650 is said by the manufacturer to be about 29:71, and the Brookfield viscosity is about 8000 (toluene solution, cps at 77° F., 25%w). The Shore A hardness is about 75.

A preferred optional diblock copolymer is Kraton® G-1702.

In a particularly preferred embodiment of the invention, the composition comprises a Kraton® triblock copolymer as described herein in combination with an oil, particularly natural or synthetic white oils which are known as having a smooth homogeneous consistency.

The candles of the invention are prepared by blending into the hydrocarbon oil one or more triblock, radial block and/or multiblock copolymers, or mixtures thereof, in the desired amount. A diblock copolymer may also be optionally included. The amount of each copolymer and the amount of the mixture contained in the hydrocarbon oil determines the final form of the gel. In general, the higher the copolymer content, the stiffer the gel. The gels under the present invention are firm, transparent gels.

The candle is formed by blending the polymers and oil and heating the mixture to from about 50° C. to about 150° C. to dissolve the copolymer or copolymer blend in the oil. Mixing may be carried out in any conventional manner, and is preferred, particularly when colorants, fragrances, etc. are added. On cooling, a stiff, clear gel forms. Preferably, a wick is added while the composition is in melted form. Alternatively, a formed gel can be heated, the wick added, and the gel allowed to reform on cooling.

In yet another embodiment of the invention, the hydrocarbon oil is first heated to from about 50° C. to about 150° C., at which point the copolymer mix is added to the desired weight percent as set forth herein. After sufficient time for the copolymer to melt in the oil, the composition is poured into a mold or a jar either containing a wick or, alternatively a wick thereafter being added, and the composition is allowed to cool to a stiff gel. Similar variations of the method of the invention and known to the skilled person in light of the present disclosure are within the scope of the present invention.

Particularly preferred in making the candles of the invention is to cool the polymer composition in a mold or jar. A mold is used to impart external features to, for example, a pillar candle, if desired. Conventional jars, clear, colored or otherwise decorative, such as sculpted, etched, cut glass, etc., are also usefully employed for holding candles under the invention. Preferably, clear glass jars are used for a jar candle.

Shown in FIG. 1 is a transparent glass jar candle 1 under one embodiment of the invention. The candle is a clear glass jar 3, containing a transparent, stiff, thermally reversible mineral oil gel 5, and a wick 7.

The candles employ a wick, typically of porous material, which may be either waxed or unwaxed, and of the thickness appropriate for the particular candle design. The wicks used are conventional and are well known to those of ordinary skill in the art. The wick may include a decorative feature, for example, striping, coloring, impregnation or coated with material for special effects, such as to provide a colored flame, sparkles, etc., if so desired.

The candles of this invention may also contain one or more conventionally employed additives such as stabilizers, anti-oxidants, colorants, fragrances, and the like to an extent not affecting or decreasing the desired properties of the candle. With respect to anti-oxidants, specific reference is made to BHT, which is generally employed at about 0.01 weight percent.

Colorants are useful in the invention when desired, as the gel composition is generally transparent. Thus, the candles of the invention can range from completely colorless and transparent to having a deep color, as desired, by control of the amount of colorant, if any, employed. The candles may also be multicolored or have colored layers. The latter is achieved by forming one colored layer, allowing the layer to cool, and overlaying with a second colored layer, and so on.

Other designs can be employed, such as single or multi color swirls. Such swirls can be achieved by adding the color to the gel composition at a time during cooling of the composition but prior to complete gelation, and gently stirring the composition. Similar design variations will be readily apparent to those skilled in the art in light of the present disclosure, and are meant to be within the scope of the invention.

An additional decorative benefit of the candle under the invention is that ornamental features may be embedded within the candle body. Such features may be either insoluble or soluble in the gel composition of the candle, as desired. Use of such ornamental features allows a possibility not heretofore available in decorative features, as virtually any decorative object can be incorporated within the candle body, provided generally that such decorative feature does not adversely affect the burning capacity of the candle in an undesired way.

Notwithstanding the above, decorative and other functional features that interfere with the burning of the candle may be incorporated in the candle under the invention, if so desired. For example, in suitable candle designs, decorative features located near the periphery of the candle and not in communication with the wick or flame will not adversely affect the operation of the candle and may thus be of any sort desired. Such a decorative feature may be placed in the candle, for example, by addition to the gel composition after sufficient cooling of the melt but before complete gelation.

Exemplary insoluble decorative features include stars, glitter, sparkles, ribbons, etc.

Other decorative additives, such as those that cause special effects, e.g. sparkling, flame coloring, etc., or mixtures thereof, may also be added to the gel composition of the candle in conventional amounts and as desired.

Fragrances, for example, cinnamon, spice, bayberry, pine, essence oils, etc., are also useful in the candles of the invention, in a manner similar to the way conventional wax candles employ pleasing aromatic additives. Conventional oil based, solid and other fragrances are available and known to the person skilled in the art. These fragrances can be employed by inclusion into the oil of the composition under the invention. Alternatively, if the fragrance is particularly volatile, it is preferably added to the cooling composition prior to complete gelation.

Fragrances are generally employed at up to about 20% by weight of the total gel composition. However, it is recognized by those skilled in the art that fragrant additives can be used up to their characteristic solubility level in the composition of the candle of the invention. Accordingly, the invention as presently claimed is not limited with respect to the weight percent of a particular fragrant additive.

The candles under the invention may also contain a functional additive, such as an insect repellant, for use in the same capacity as conventional candles containing such an additive. These additives are used in the conventional amounts under the invention, as known to the person skilled in the art. U.S. Pat. No. 5,387,418, for example, discloses one such insect repellant compound that may be employed in the candle of the invention. Citronella oil is another example of an insect repellant that may be used under the invention.

As example of another functional additive, one may place a flame retardant in the candle, located at suitable location so as to automatically extinguish the candle at that location. Thus, if it is desired that the candle self-extinguish at, for example, one inch from the bottom, a first layer of the composition of the invention including a flame retardant may be poured to the one inch height. After cooling of said first layer, a subsequent layer of the gel composition lacking the flame retardant can be layered over the first layer. In operation, the candle burns normally until reaching the area in which the flame retardant has been incorporated, at which point the candle self extinguishes. Flame retardants are known to those skilled in the art and are used at conventional levels.

In preparation of the candles under the invention, where possible, additives are most preferably added to the hydrocarbon oil in the desired amount. Additives may also be added during mixing of the base candle composition or while said composition is cooling to a gel.

The following examples are presented to illustrate the invention but it is not to be considered as limited thereto. In the examples parts are by weight unless otherwise indicated.

In these examples, the diblock and triblock polymers used are Kraton® polymers obtained from Shell Chemical Company.

EXAMPLE 1

Kraton® thermoplastic rubbers were dissolved in Drakeol-7 in various combinations and at various percentages. These gels were prepared by dissolving the block copolymers indicated in the mineral oil at about 50° C.–120° C. The solutions were then poured into clear glass jars and allowed to cool. Results are given in Table 1.

TABLE 1

| Blend Number | Diblock (wt %) (Kraton G-1702) | Triblock (wt %) (Kraton G-1650) | Mineral Oil (wt %) | BHT (wt %) |
| --- | --- | --- | --- | --- |
| 1 | 0 | 5 | 94.99 | 0.01 |
| 2 | 0 | 20 | 79.99 | 0.01 |
| 3 | 5 | 5 | 89.99 | 0.01 |
| 4 | 5 | 20 | 74.99 | 0.01 |
| 5 | 0 | 2 | 97.99 | 0.01 |
| 6 | 0 | 3 | 96.99 | 0.01 |

TABLE 1-continued

| Blend Number | Diblock (wt %) (Kraton G-1702) | Triblock (wt %) (Kraton G-1650) | Mineral Oil (wt %) | BHT (wt %) |
|---|---|---|---|---|
| 7 | 0 | 4 | 95.99 | 0.01 |

Each of the blends were found to provide firm, transparent gels, except for blends 5 and 6, which were solid (non-pourable) but soft gels and were slightly translucent. Gels 2 and 4 were very hard.

EXAMPLE 2

A blend is prepared having about 84.99 weight percent Drakeol® 7, about 15 weight percent Kraton® 1650 triblock copolymer and about 0.01 weight percent BHT and processed as in Example 1. As cooling proceeded, the composition is poured into a glass jar and a standard candle wick is added to the gel and held in place until the gelation is complete. The resultant candle is clear, and burns evenly for several hours.

EXAMPLE 3

A blend is prepared having about 89.99 weight percent Drakeol® 7, about 8 weight percent Kraton® 1650 triblock copolymer, about 2 weight percent Kraton-G® 1702 diblock copolymer and about 0.01 weight percent BHT and processed as in Example 2. As cooling proceeded, the composition is poured into a transparent, green glass jar and a standard candle wick is added to the gel and held in place until the gelation is complete. The resultant candle is clear within the decorative jar, and burns evenly for several hours.

EXAMPLE 4

A blend is prepared having about 87.49 weight percent Drakeol® 7, about 8 weight percent Kraton® 1650 triblock copolymer, about 4.5 weight percent Kraton-G® 1702 diblock copolymer and about 0.01 weight percent BHT and processed as in Example 2. Prior to cooling, the composition is poured into a clear glass jar and a standard candle wick is added to the gel and held in place until the gelation is complete. The resultant candle is clear within the jar, and burns evenly for several hours.

EXAMPLE 5

A blend was prepared having about 91.39 weight percent Drakeol® 7, about 8.5 weight percent Kraton® 1650 triblock copolymer, about 0.1 weight percent Kraton-G® 1702 diblock copolymer and about 0.01 weight percent BHT and processed as in Example 2. Prior to cooling, the composition was poured into a clear glass jar and a standard candle wick is added to the gel and held in place until the gelation is complete. The resultant candle is clear within the jar, and burns evenly for several hours.

EXAMPLE 6

A blend is prepared having about 91.99 weight percent Drakeol® 7, about 8 weight percent Kraton® 1650 triblock copolymer and about 0.01 weight percent BHT and processed as in Example 2. Prior to cooling, the composition is poured into a clear glass jar and a standard candle wick is added to the gel and held in place until the gelation is complete. The resultant candle is clear within the jar, and burns evenly for several hours.

The invention has been described herein with reference to certain preferred embodiments. However, as obvious variants thereon will become apparent to those skilled in the art, the invention is not to be considered as limited thereto.

We claim:

1. An article of manufacture comprising a candle, said candle consisting essentially of a gel consisting essentially of from about 70% to about 98% by weight of a hydrocarbon oil, and from about 2% to about 30% by weight of a triblock copolymer, and having a wick in said gel, and said candle optionally containing one or more additives selected from the group consisting of an antioxidant, stabilizer, fragrance, colorant, insect repellent, and flame retardant.

2. The article of manufacture according to claim 1, wherein the candle is contained in a jar.

3. The article of manufacture according to claim 1, wherein said candle additionally contains an anti-oxidant.

4. The article of manufacture according to claim 1, wherein said candle additionally contains a fragrance.

5. The article of manufacture according to claim 1, wherein said candle additionally contains a colorant.

6. The article of manufacture according to claim 1, wherein said candle additionally contains an insect repellant.

7. The article of manufacture according to claim 1, wherein said gel consists essentially of from about 85% to about 98% by weight of a hydrocarbon oil, and from about 2% to about 15% by weight a copolymer consisting essentially of a triblock copolymer.

8. The article of manufacture according to claim 1, wherein said gel consists essentially of from about 93% to about 80% by weight of a hydrocarbon oil, and from about 7% to about 20% by weight a copolymer consisting essentially of a triblock copolymer.

9. The candle according to claim 8, wherein said candle is a jar candle.

10. The candle according to claim 1, wherein said candle is transparent and further optionally contains in said candle a decorative material selected from the group consisting of insoluble stars, flitter, sparkles, and ribbons.

* * * * *